US00PP36862P2

(12) United States Plant Patent
Hansoti

(10) Patent No.: US PP36,862 P2
(45) Date of Patent: Jul. 22, 2025

(54) ***SANSEVIERIA* PLANT NAMED 'Hansoti60'**

(50) Latin Name: ***Sansevieria* hybrid**
Varietal Denomination: Hansoti60

(71) Applicant: Ashish Hansoti, Mumbai (IN)

(72) Inventor: Ashish Hansoti, Mumbai (IN)

( * ) Notice: Subject to any disclaimer, the term of this patent is extended or adjusted under 35 U.S.C. 154(b) by 0 days.

(21) Appl. No.: 19/000,683

(22) Filed: Dec. 23, 2024

(51) Int. Cl.
*A01H 5/02* (2018.01)
*A01H 6/12* (2018.01)

(52) U.S. Cl.
USPC ..... Plt./382
CPC ..... *A01H 6/12* (2018.05)

(58) Field of Classification Search
USPC ..... Plt./382
CPC ..... A01H 5/02
See application file for complete search history.

*Primary Examiner* — Kent L Bell

(57) ABSTRACT

A new and distinct cultivar of *Sansevieria* plant named 'HANSOTI60' is disclosed, characterized by unique terete light grey-green foliage with darker green linear markings in the form of green rings or bands along the circumference of the leaf, contrasting with the light silvery-grey-green background. Tips are somewhat stiff, soft, and non-aggressive. 'Hansoti60', unlike most commercial *Sansevieria* cultivars known to the Inventor, comes true to type from adventitious shoots from leaf cuttings and the resulting pups are of a rosette form even when just few weeks old and quite small so they can be used in various smaller size pots Overall, 'Hansoti60' presents as a silvery light grey-green, rather stiff, terete leaved pot plant. The new cultivar can be classified in the "Novelty *Sansevieria* Group". The new variety is a *Sansevieria*, typically produced as an ornamental plant.

7 Drawing Sheets

Figure 1:
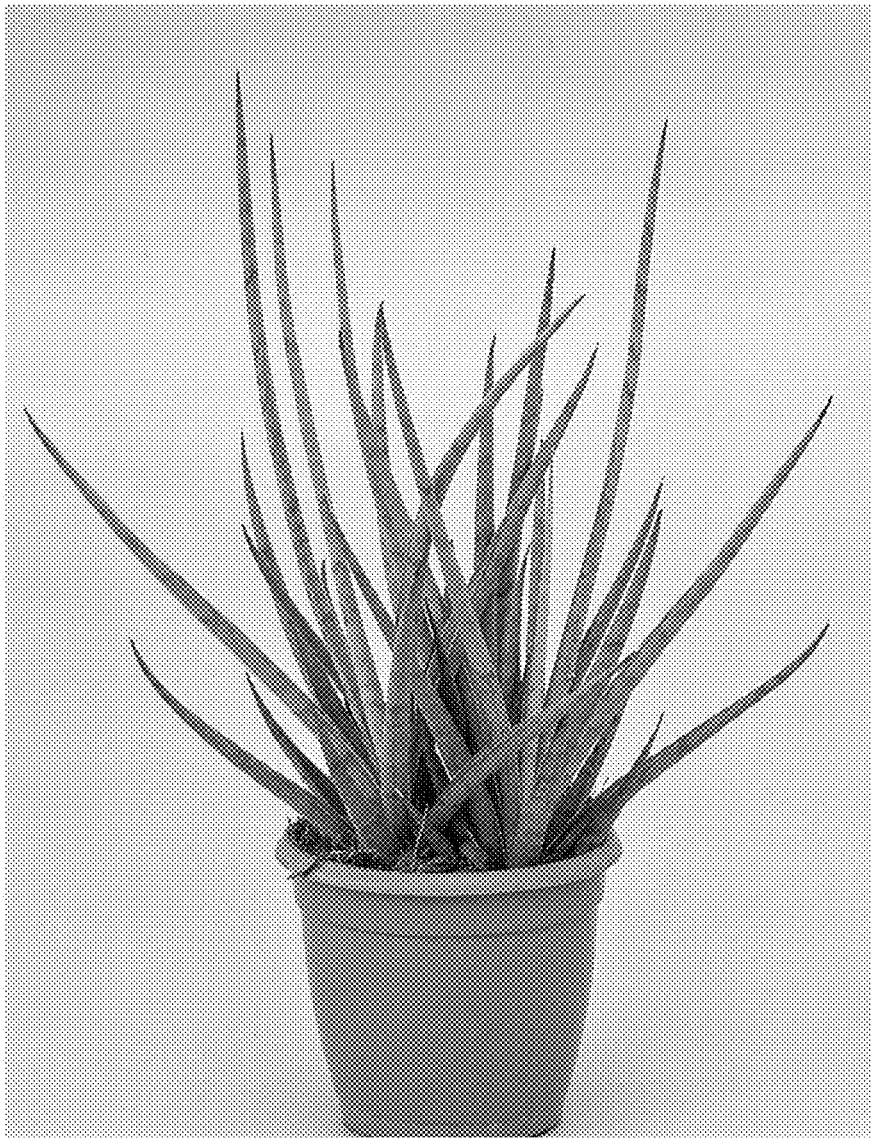

Latin name of the genus and species: *Sansevieria* hybrid. Variety denomination: 'HANSOTI60'.

BACKGROUND OF THE INVENTION

The present invention relates to a new and distinct cultivar of *Sansevieria* plant, botanically known as *Sansevieria*, of the family Asparagaceae, hereinafter referred to by the cultivar name 'HANSOTI60'.

*Sansevieria* is a monocotyledonous plant with fleshy, succulent leaves which are available in a huge range of species, varieties and cultivars as an outdoor ornamental plant (under tropical conditions) or as indoor plants.

The new *Sansevieria* 'Hansoti60' was discovered and selected by Mr. Ashish Hansoti, as a chance seedling from open pollinated seeds on a non-patented cultivar of *Sansevieria bacularis* 'Mikado' aka 'Fernwood' in the USA, flowering on the breeders' research tables. Pollen parent was unknown (i.e. a seedling from open pollinated seeds) at Village Asle, District Satara, Maharashtra State in Western India during January 2019.

Asexual reproduction of the new *Sansevieria* cultivar by side shoots as well as leaf cuttings was first performed in June-July 2020 in Village Asle, District Satara, Maharashtra State in Western India and it was seen that the distinctive combination of characteristics of the new cultivar reproduced true to type from basal suckers as well as from leaf cuttings.

The discovery (sometime in autumn 2020) that the variety 'Hansoti60' came true to type from leaf cuttings was a breakthrough as not only did it mean much quicker propagation but also the production of smaller plants with good rosette shape at an early stage which were suitable for small pots and which developed a good plant form when grown in smaller pots such as 9 cm pots.

BRIEF SUMMARY OF THE INVENTION

The following traits have been repeatedly observed and are determined to be unique characteristics of 'HANSOTI60', which in combination distinguish this *Sansevieria* as a new and distinct cultivar:

1. Unique terete light grey-green foliage with darker green linear markings in the form of green rings or bands along the circumference of the leaf, contrasting with the light silvery-grey-green background. Overall, 'Hansoti60' presents as a silvery light grey-green, rather stiff, terete leaved pot plant. Commercially this plant is best grown as a 3PP (3 Plants per Pot) to give enough "volume" to fill the pot.
2. The leaves are almost entirely round in cross section (terete) except for a shallow sulcus at the proximal half of the leaf, fleshy, with maximum diameter up to 10 mm, upright, somewhat stiff but with soft, non-aggressive tips that do not hurt or poke even in large mature plants.
3. 'Hansoti60', unlike most commercial *Sansevieria* cultivars known to the Inventor, comes true from adventitious shoots from leaf cuttings and the resulting pups are of a rosette form even when just few weeks old and quite small so they can be used in various smaller size pots. In contrast, when grown from side shoots, by the time that the pups attain a nice rosette form, they are invariably too large for pots of 6 cm to 10 cm or smaller. Typically, for this cultivar, 3 Plants per Pot (3PP) are used to give a full pot plant.

4. 'Hansoti60' is an extremely tough plant, even when compared to other *Sansevieria* cultivars known to the Inventors, with practically no pests or disease problems.

The new variety 'HANSOTI60' is considered a variety of *Sansevieria* in the group denominated as the "Novelty *Sansevieria* Group". The new variety presents an average of 7 to 9 leaves per plant when it reaches its saleable size (between 3 to 4 months from rooted liner depending on finished pot size). The new variety has a upright growth habit and the entire plant can reach a height ranging between 18 and 22 cm in a 9 cm pot, and 30 to 35 cm when grown in a 12 cm pot. The leaves are narrow with maximum diameter of about 10 mm and terete with a smooth texture and waxy feel. The blades are thick and fleshy. This variety rosette also has an inverted triangle shape.

The new variety is very heat tolerant and adapts well to conditions of bright light and heavy shade (exterior and interior).

The new variety is moderately drought tolerant and adapts well to conditions of bright light and heavy shade (exterior and interior).

The main color of a recently mature leaf is a silvery green near RHS Green 138B to 139C with darker annular rings which are equivalent to cross hatching seen in many *Sansevieria*, especially *S. trifasciata*. The color of these annular rings is near Green 139A.

Attached color pictures are a better guide to the overall variegation and coloration.

PARENTAL COMPARISON

Plants of the new *Sansevieria* 'HANSOTI60' are similar to plants of the parental cultivar, however, 'HANSOTI60' differs in the characteristics described in Table I.

TABLE I

Comparison of Seed Parent & the New variety 'Hansoti60'

| | Characteristic | *Sansevieria bacularis* 'Mikado' aka 'Fernwood' | New cv *Sansevieria* hybrid 'Hansoti60' |
|---|---|---|---|
| 1. | Leaf size | 20-25 cm long (in 12 cm pot) and up to 15 mm wide. | 30-37 cm long (in 12 cm pot) but narrower - around 10 mm maximum diameter. |
| 2. | Number of leaves | 10 to 12 leaves per individual plant | 15 to 20 leaves (more than seed parent cultivar) per individual plant |
| 3. | Leaf morphology | Leaves are semi-terete but with a sulcus or channel that runs along almost full length of the leaf. The channel is slightly deep. | Leaves are terete - almost entirely cylindrical - and the sulcus or channel is only present at the proximal half or a little more of the leaf. The channel is very shallow. |
| 4. | Leaf color | Dark green with very prominent, annular light green/dark green striations commonly seen in many *Sansevieria* | Silver-green overall with subtle green striations forming rings or bands around the leaf. |
| 5. | Other differences | Overall, the plant rosette is more reflexed as the leaf tends to curve outwards. *S. bacularis* 'Mikado' is somewhat faster growing compared to 'Hansoti60'. | The rosette is more compact as each leaf is straighter and stiffer with only a little outward bending. *S. hybrida* 'Hansoti60' is slightly slower growing than its parent, *S. bacularis* 'Mikado'. |

'Hansoti60' is therefore a substantially different looking cultivar compared to the parent *S. bacularis* 'Mikado' except that both have narrow, cylindrical or terete leaves held more or less vertically and softer leaves than the typical *Sansevieria* of the "Compact *Sansevieria* Group" known to the Inventor.

Overall growth pattern in terms of relatively vertical growing leaves, softer than usual leaf substance are similar between the two cultivars.

COMMERCIAL COMPARATOR

Plants of the new *Sansevieria* 'HANSOTI60' are similar to the commercial variety *Sansevieria* 'Hansoti26', U.S. Plant Pat. No. 33,149. However, 'HANSOTI60' differs in the characteristics described in Table II.

TABLE II

Comparison of Similar S. 'Hansoti26'- U.S. Plant Pat. No. 33149 & New variety 'Hansoti60'

| | Characteristic | *Sansevieria* 'Hansoti26'- U.S. Plant Pat. No. 33149 | New cv 'Hansoti60' |
|---|---|---|---|
| 1. | Leaf Habit & number | 'Hansoti26' has much flatter leaves. Number of leaves is 10-12, fewer than 'Hansoti60' | Much more terete leaves almost circular in cross section with a short sulcus on the proximal end of the leaf. Number of leaves is 15-20, much more than 'Hansoti26' |
| 2. | Leaf Color | Overall coloration is much darker green with distinct cross hatching and prominent linear lines and markings. | Overall coloration is much lighter silvery grey-green with darker circular green rings around the leaf and no linear lines. |
| 3. | Leaf size & morphology | Leaves are longer and more recumbent. Each leaf curves gently outwards. Leaf width is 12 to 15 mm. The channel is very open, & runs the whole length of the leaf. | Leaves are shorter and more upright. Individual leaf is almost straight. Lead diameter is around 10 mm. The channel is shallow and present only in the proximal half of the leaf. |
| 4. | Plant Growth Habit | 'Hansoti26' is faster growing compared to 'Hansoti60' | 'Hansoti60' is slower growing than 'Hansoti26' |
| 5. | Plant Vigor | Somewhat more vigorous, giving pups from leaf cuttings quicker and also faster subsequent growth. | Somewhat less vigorous, taking longer to produce pups from leaf cuttings and slower subsequent growth. |

'Hansoti26' is faster growing compared to 'Hansoti60' in both, speed of propagation and in subsequent growth from liners to finished potted plant.

BRIEF DESCRIPTION OF THE PHOTOGRAPHS

The accompanying photographs illustrate the overall appearance of the new *Sansevieria* cultivar 'HANSOTI60' showing the colors as true as is reasonably possible with colored reproductions of this type. Colors in the photographs may differ slightly from the color value cited in the detailed botanical description which accurately describe the color of 'HANSOTI60'.

These pictures illustrate the plant form which is the unique characteristic of 'HANSOTI60' and at the same time demonstrates that plant coloration and variegation pattern is similar to several other *Sansevieria* cultivars. All plants were grown in an open poly house (high tunnel) at Village Asle, District Satara, Maharashtra State in Western India. Average temperature in Asle is 25° C. with summer highs of 39° C.

and winter lows of 6° C. Plants grow under natural light conditions and between 30% to 75% shade levels depending on the season (higher shade in hot summer conditions). These conditions closely approximate those used in commercial practice in India.

FIG. 1 *Sansevieria* 'Hansoti60' a 3PP (Three Plants per Pot) finished plant in 12 cm pot. This is how this cultivar is typically grown.

Figure 2:
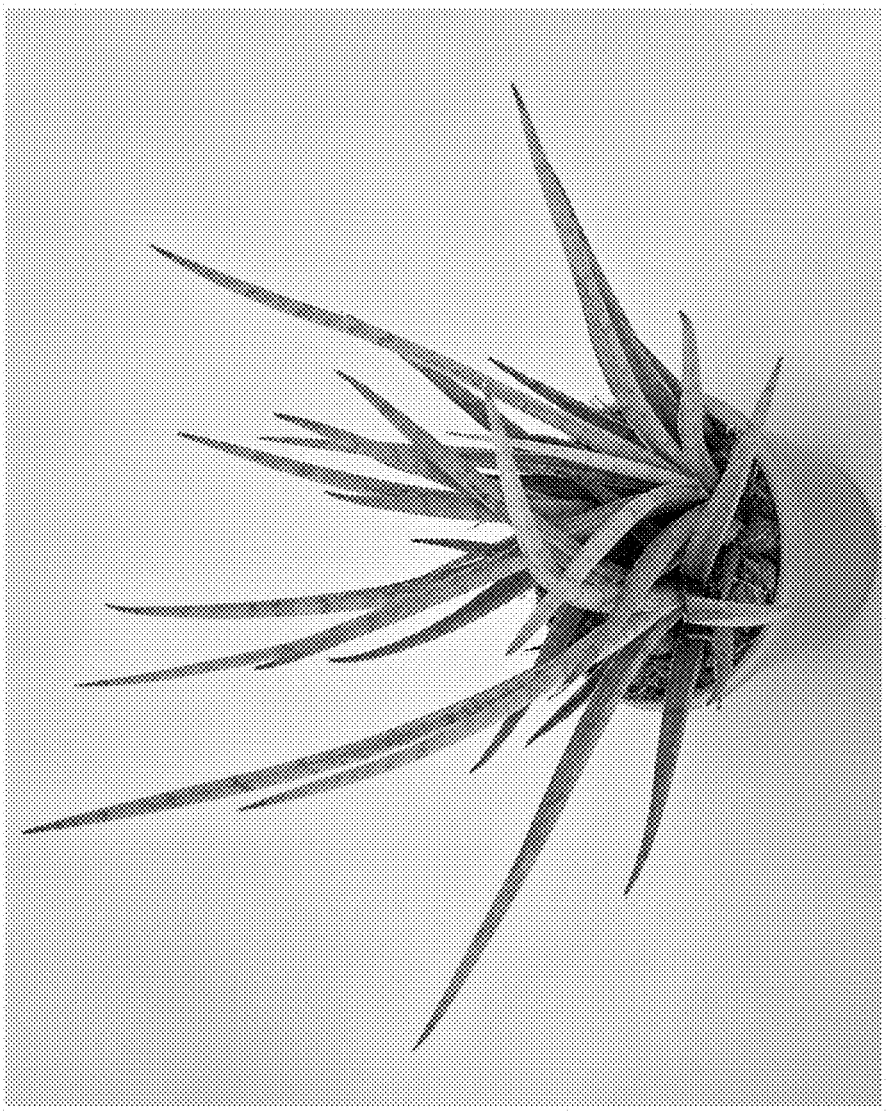

FIG. 2: *Sansevieria* 'Hansoti60' a 3PP (Three Plants per Pot) finished plant in 12 cm pot, top view.

FIG. 1 and FIG. 2 show two views of a three- to four-month-old (from rooted liner) potted plant of *Sansevieria* 'Hansoti60' in a 12 cm diameter pot. Commercially this cultivar is planted as a 3 Plants Per Pot clump (3PP) to give a fuller potted plant.

Figure 3:
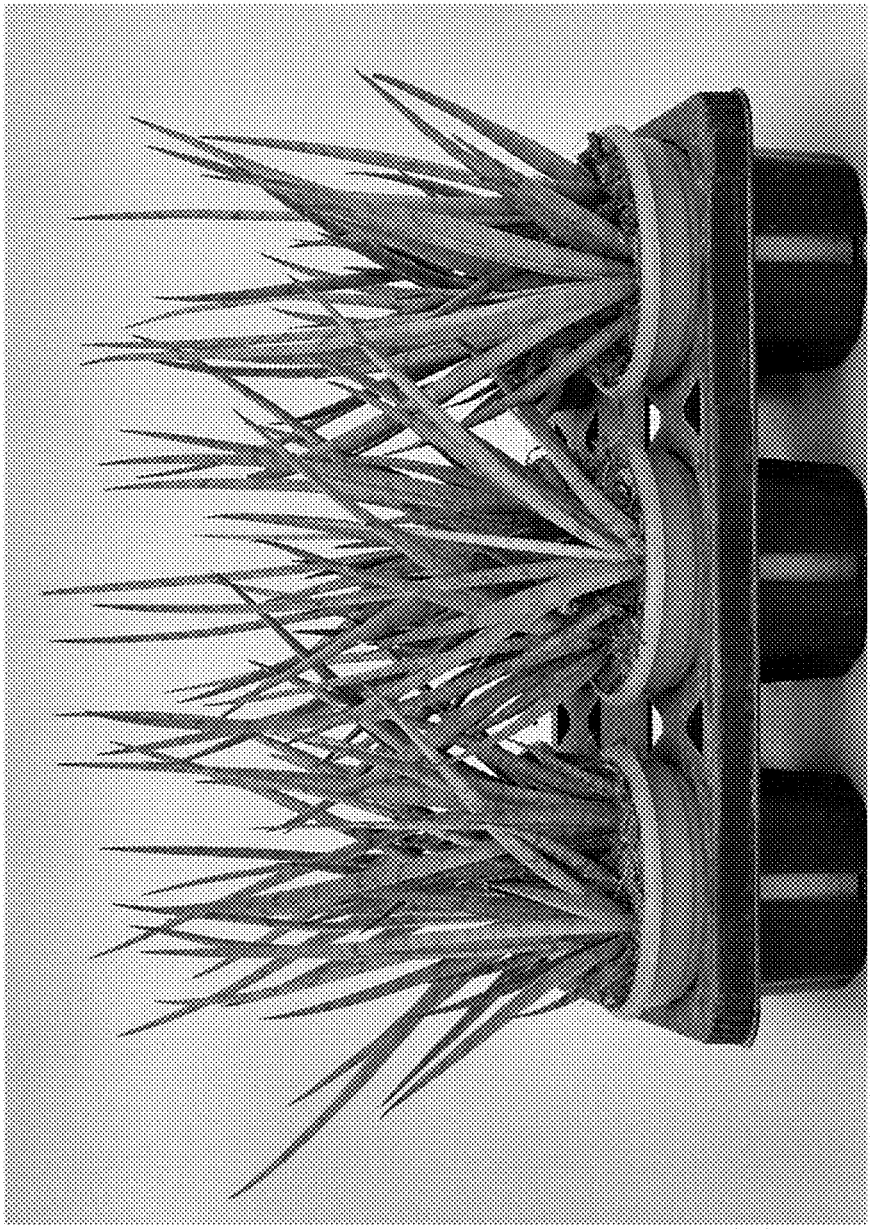

FIG. 3: Shows a tray with 6 12 cm pots, 3PP, showing very uniform color, leave arrangement and form across multiple plants.

Figure 4:
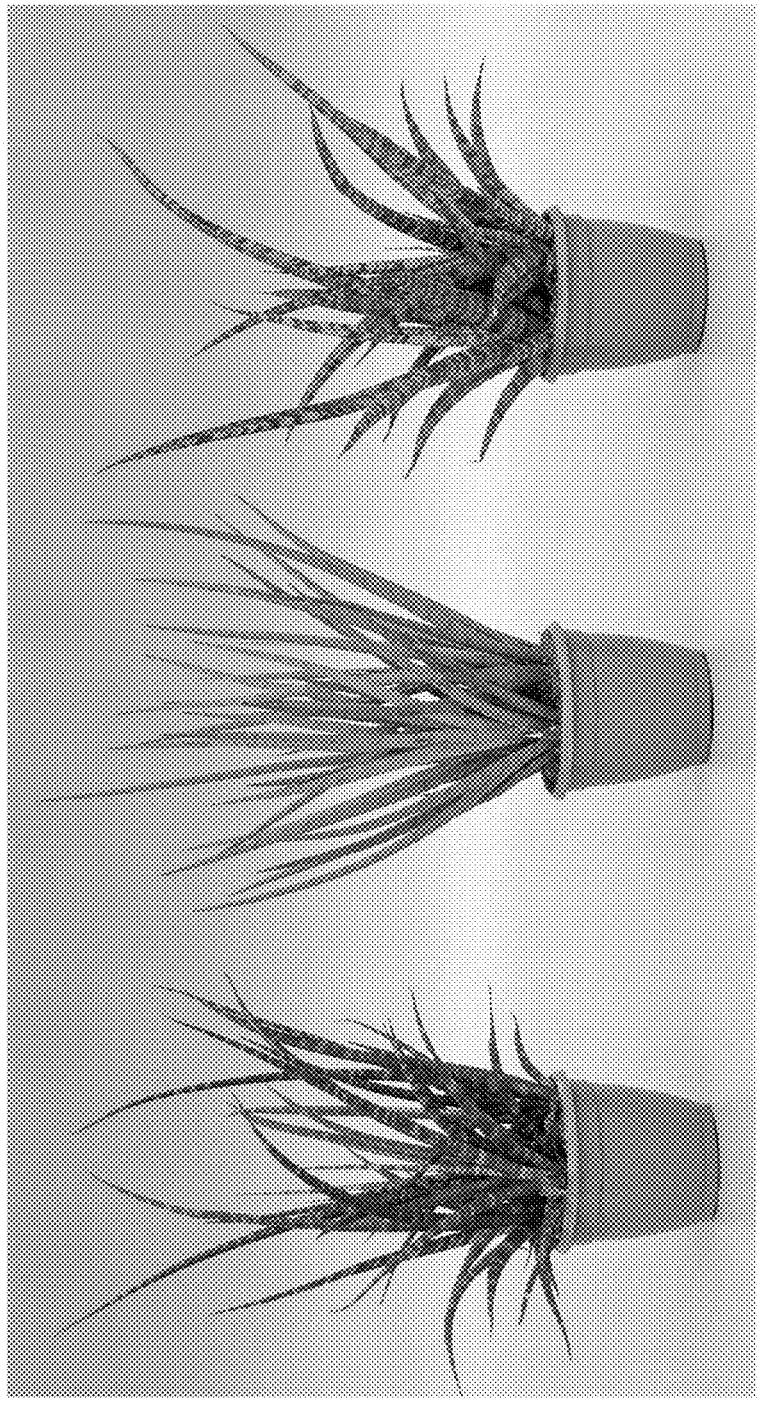

FIG. 4: Shows *Sansevieria* 'Hansoti60' (center) together with both the other cultivars the seed parent *Sansevieria bacularis* 'Mikado' (far left) and *Sansevieria* hybrid 'Hansoti26' (far right) as the comparison cultivar. All pots have 3 Plants per Pot (3PP) planted to give a full and commercially acceptable potted plant.

Figure 5:
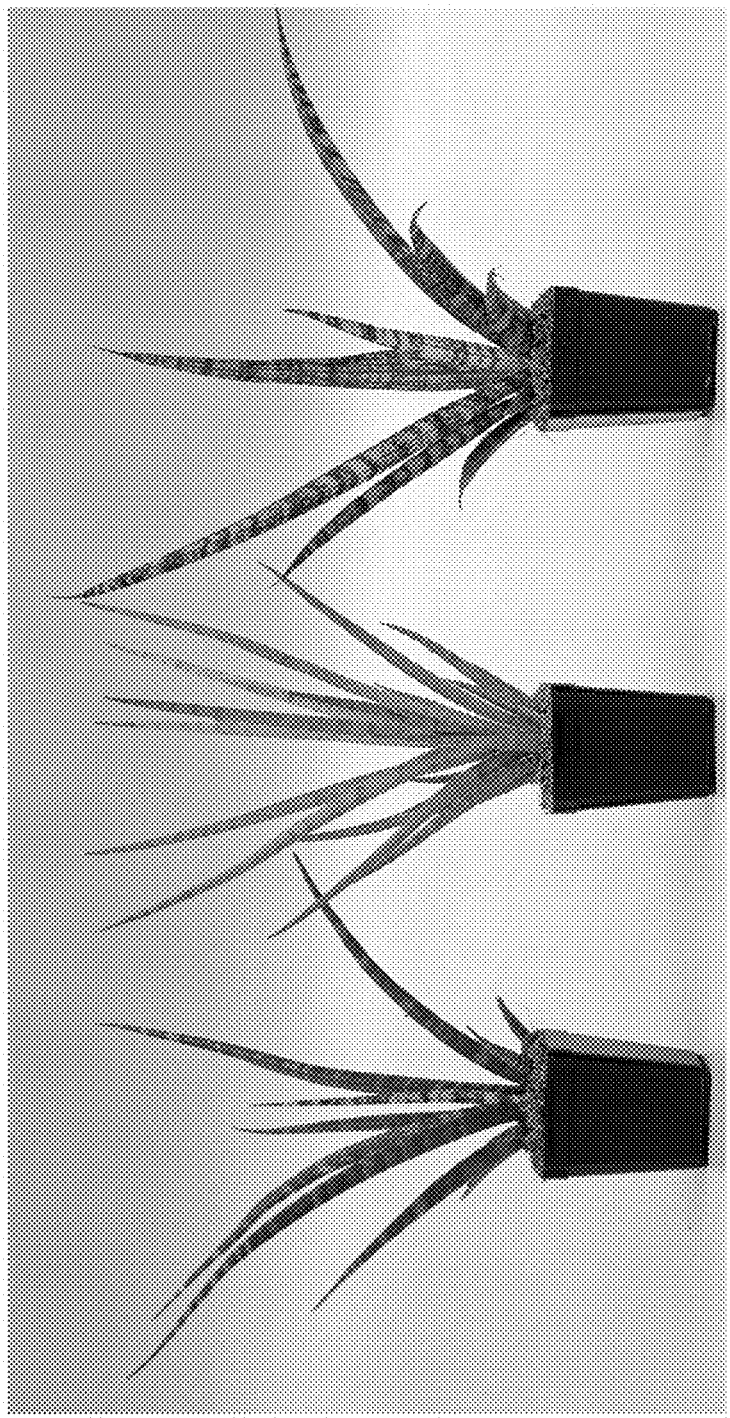

FIG. 5: Shows the same 3 cultivars as FIG. 4 but single plants in small, 6.5 cm square pots. Individual plants allow an improved comparison of the plants than 3PP pots in FIG. 4.

Figure 6:
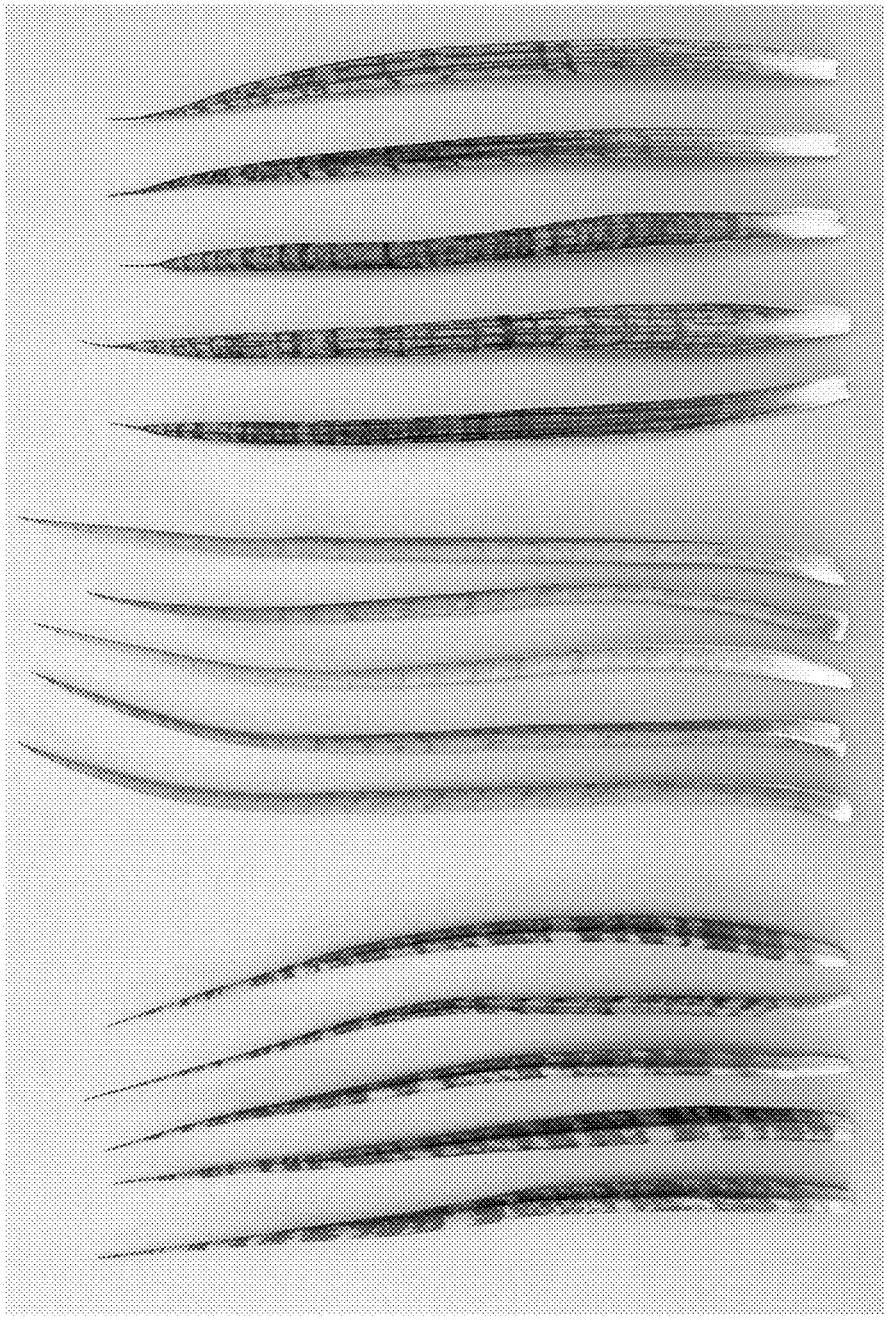

FIG. 6: Individual leaves from the same 3 cultivars above, showing the differences in color and curvature. 'Hansoti60' (center), 'Mikado' (left) and 'Hansoti26' (right).

Figure 7:
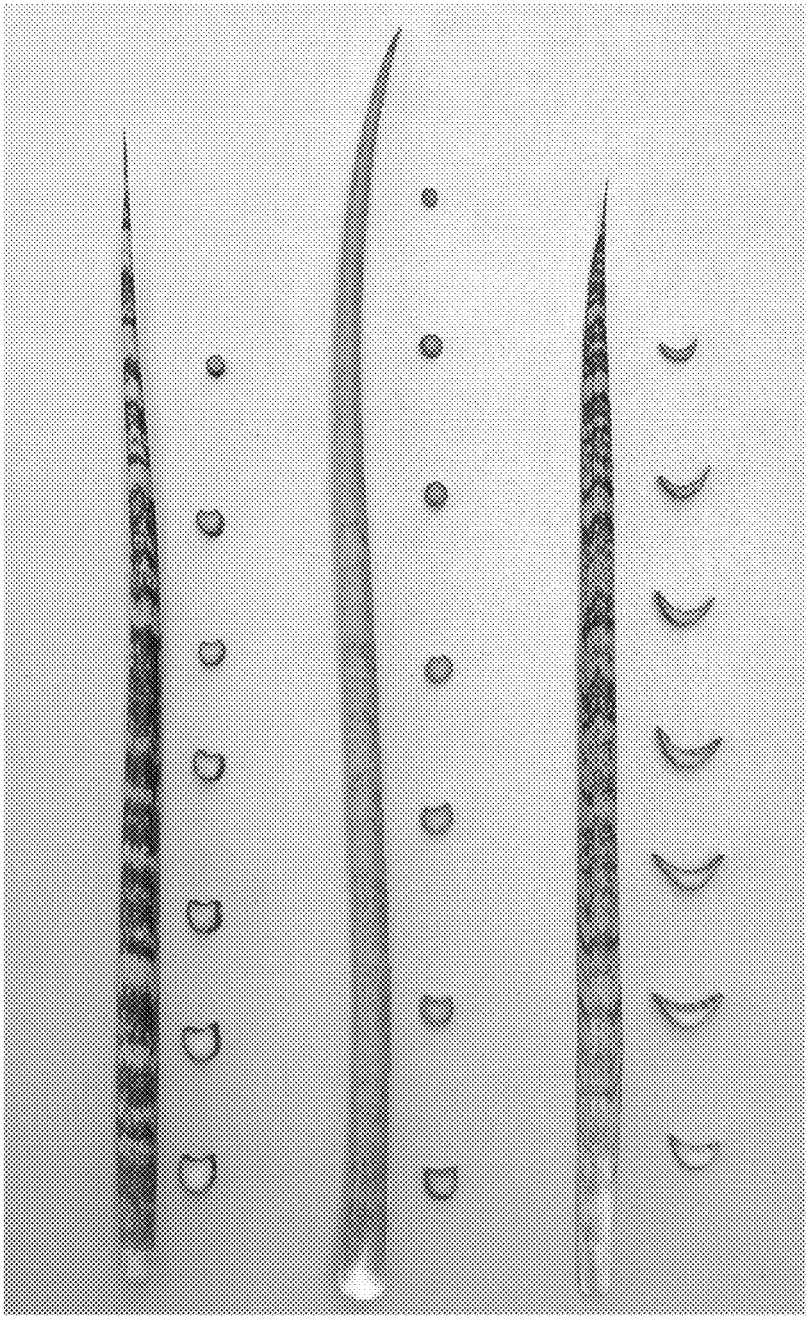

FIG. 7: Single leaf of each of the three cultivars above, sliced at various levels along the length of the leaf to show its shape in cross section, clearly illustrating how terete each leaf is as well as where the sulcus starts and ends. 'Hansoti60' (center), 'Mikado' (left) and 'Hansoti26' (right).

DETAILED BOTANICAL DESCRIPTION

The new *Sansevieria* 'HANSOTI60' has not been observed under all possible environmental conditions. The phenotype of the new cultivar may vary with variations in environment such as temperature, light intensity, fertilizer levels and composition and day length without any change in the genotype of the plant.

The aforementioned photographs, together with the following observations, measurements and values describe the new *Sansevieria* cultivar 'HANSOTI60' plants grown in an open poly house (high tunnel) at Village Asle, District Satara, Maharashtra State in Western India. Average temperature in Asle is 25° C., with summer highs of 39° C. and winter lows of 6° C. Plants grow under natural light conditions and between 30% to 75% shade levels depending on the season (higher shade in hot summer conditions).

This crop gets nearly constant fertilization to increase production. Controlled release fertilizer of 13:11:11 Type 360-days release at 1 kilo/cubic meter of media, constant liquid feed at approximately 150 ppm N, 30 ppm P and 150 ppm K, along with complete micronutrients. Production is closely regulated with proper and complete plant nutrition and an open soilless growing media based on coconut coir. The plants are grown in plastic pots on metal benching in spacing trays.

Color references are made to The Royal Horticultural Society Colour Chart (R.H.S.), (April 2009) except where general colors of ordinary significance are used.

The photographs and descriptions were taken during the winter season in Asle, District Satara, Maharashtra State, India when outdoor day temperature was 25° C. to 30° C. and cool nights, usually of 10° C. to 15° C. The age of the plants described is 3-4 months from pups harvested from leaf cutting community pots, in 12 cm pots.

Botanical classification: *Sansevieria* hybrid 'HANSOTI60'.

General information:

*Parentage*.—Seed parent: *Sansevieria bacularis* 'Mikado', unpatented. Pollen parent unknown.

*Optimal growth conditions*.—

*Light intensities*.—High adaptability to outdoor or indoor conditions.

*Temperature*.—Day: 25° C. to 35° C. Night: 15° C. to 25° C.

*Temperature tolerance*.—Tolerant to a low temperature of about 6° C. and a high temperature of 38° C. and above — very heat tolerant.

*Fertilization*.—Constant feed of 150 ppm N, 30 ppm P and 150 ppm K is used along with micronutrients with occasional leaching. Slow-release 13:11:11 added at 1 kg/cubic meter of growing media.

*Growth regulators*.—Not necessary for growing this selection.

Propagation:

*Typical*.—Vegetative, by leaf cuttings — unlike most *Sansevieria* cultivars, 'Hansoti60' comes true to type from leaf cuttings. Propagation using side shoots or suckers also possible.

*Rooting habit and description*.—Leaf cuttings root easily and subsequently give adventitious shoots (pups) from the cut edge of the leaf cutting.

*Time to initiate roots*.—45 to 60 days at 25° C. to 30° C.

*Time to produce a rooted liner*.—About 90 to 120 days at 25° C. to 30° C.

*Time to produce ready* 12 *cm potted plant*.—About 3 months at 25° C. to 30° C. from pups obtained from leaf cutting community pots.

Plant:

*General appearance and form*.—Monocot; leaf bases arranged in a rosette around growth point.

*Height*.—About 30 to 35 cm when grown in 12 cm pots.

*Spread*.—About 35 to 40 cm when grown when grown in a 12 cm size container.

*Growth rate and habit*.—Reasonably fast growing; upright.

*Shape*.—Inverted triangle.

*Fragrance*.—None.

*Stem*.—Modified (rhizomes with erect foliage).

*Rosette height*.—About 18 to 22 cm in a 9 cm pot, and 35 to 40 cm when grown in 12 cm size container.

*Rosette diameter*.—About 35 to 40 cm.

*Texture*.—Smooth, waxy.

*Color*.—As described above.

*Strength*.—Strong and durable.

*Internode length*.—About 1 mm.

Foliage:

*Quantity*.—About 15 to 20 leaves, or more with age.

*Arrangement and attachment*.—Rosulate; leaf bases arranged in a rosette around central growth point.

*Leaf length*.—Varies from 30 to 37 cm in a plant finished in a 12 cm pot.

*Leaf width*.—About 10 cm at widest point.

*Overall shape of leaf*.—Lanceolate.

*Channel or sulcus*.—Shallow, only on proximal half of the leaf.

*Apex shape*.—Aristate but soft and safe to touch. Not particularly brittle so plants not easily damaged on handling.

*Base shape*.—Decurrent.

*Margin*.—Entire.

*Texture*.—Upper Surface: Smooth and waxy texture.

*Texture*.—Under Surface: Slightly rough with a distinctly matte texture.

*Pubescence*.—None.

*Color of mature leaf*.—Silvery grey-green color near RHS Green 138B to 139C with cross bands along leaf circumference near Green 139A. Lower surface nearer Green 138C.

*Venation*.—Pattern: not visible on leaf surface. Longitudinal/parallel leaf shape.

*Petiole*.—Sessile leaves.

*Leaf fragrance*.—None.

Other:

*Inflorescence description*.—Flowers not observed to date.

*Weather resistance*.—Moderately drought tolerant.

*Pest resistance*.—Reasonably resistant to pests, susceptible to root mealybugs (*Rhizoecus pritchardi*). Typical pests include *Pseudococcidae longispinus* and *Tetranychus urticae*.

*Disease resistance*.—Occasionally shows *Anthracnose* and leaf spots but largely disease-free from clean mother stock and appropriate disease mitigation measures undertaken.

*Fruit/seed production*.—No fruits/seeds detected to date.

What is claimed is:

1. A new and distinct cultivar of *Sansevieria* plant named 'HANSOTI60' as herein illustrated and described.

* * * * *